(12) United States Patent
Gill et al.

(10) Patent No.: US 7,261,557 B2
(45) Date of Patent: Aug. 28, 2007

(54) PORTABLE FLUID WARMING SYSTEM

(75) Inventors: Brijesh Gill, Houston, TX (US);
Charles Cox, Bellaire, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 538 days.

(21) Appl. No.: 10/886,191

(22) Filed: Jul. 7, 2004

(65) Prior Publication Data
US 2006/0009736 A1 Jan. 12, 2006

(51) Int. Cl.
*F23D 14/12* (2006.01)
*F23D 14/14* (2006.01)

(52) U.S. Cl. ........................ 431/328; 431/329; 126/208; 604/113

(58) Field of Classification Search ........... 431/328, 431/329, 326, 268; 126/208; 604/113
See application file for complete search history.

(56) References Cited

U.S. PATENT DOCUMENTS

| | | | |
|---|---|---|---|
| 1,616,143 A | 2/1927 | Schnepp | |
| 2,904,014 A | 9/1959 | Meyers | |
| 3,590,215 A | 6/1971 | Anderson et al. | |
| 4,366,804 A | 1/1983 | Abe | |
| 4,464,563 A | 8/1984 | Jewett | |
| 4,480,631 A | 11/1984 | Kristensen | |
| 4,532,414 A | 7/1985 | Shah et al. | |
| 4,716,885 A | 1/1988 | Zaborowski | |
| 4,735,609 A | 4/1988 | Comeau et al. | |
| 4,759,749 A | 7/1988 | Verkaart | |
| 4,878,537 A | 11/1989 | Verkaart | |
| 4,900,308 A | 2/1990 | Verkaart | |
| 5,042,455 A | 8/1991 | Yue et al. | |
| 5,063,994 A | 11/1991 | Verkaart | |
| 5,097,898 A | 3/1992 | Verkaart | |
| 5,101,804 A * | 4/1992 | Cohn ................ | 126/263.01 |
| 5,245,693 A | 9/1993 | Ford et al. | |
| 5,254,094 A | 10/1993 | Starkey et al. | |
| 5,295,964 A | 3/1994 | Gauthier | |
| 5,408,576 A | 4/1995 | Bishop | |
| 5,417,274 A | 5/1995 | Verkaart | |
| 5,512,043 A | 4/1996 | Verkaart | |
| 5,544,645 A | 8/1996 | Armijo et al. | |
| 5,807,332 A | 9/1998 | Augustine et al. | |
| 5,810,779 A | 9/1998 | Baker et al. | |
| 6,142,974 A | 11/2000 | Kistner et al. | |
| 6,259,067 B1 | 7/2001 | Faries, Jr. et al. | |
| 6,294,762 B1 | 9/2001 | Faries, Jr. et al. | |
| 6,376,805 B2 | 4/2002 | Faries, Jr. et al. | |
| 6,384,380 B1 | 5/2002 | Faries, Jr. et al. | |

FOREIGN PATENT DOCUMENTS

| WO | WO 00/16722 | 3/2000 |
|---|---|---|
| WO | WO 01/62194 A1 | 8/2001 |

OTHER PUBLICATIONS http://www.hypothermia-ca.com/; printout, 2 pages.

* cited by examiner

*Primary Examiner*—Alfred Basichas
(74) *Attorney, Agent, or Firm*—Duane Morris LLP

(57) ABSTRACT

The present invention relates to a portable apparatus for warming biocompatible fluids for use in the treatment of injured patients. The present invention may be used to warm intravenous fluids for trauma resuscitation or to warm air from a ventilator circuit. The portable nature of the present invention makes it highly suitable for field applications, such as a forward surgical hospital near a combat zone.

20 Claims, 3 Drawing Sheets

PORTABLE FLUID WARMING SYSTEM

BACKGROUND OF THE INVENTION

1. Field of the Invention

The present invention relates to a portable apparatus for warming biocompatible fluids for use in the treatment of injured patients. The present invention may be used to warm intravenous fluids for trauma resuscitation or to warm air from a ventilator circuit. The portable nature of the present invention makes it highly suitable for field applications, such as a forward surgical hospital near a combat zone.

2. Description of the Prior Art

Hypothermia is quite common in injured patients, including patients experiencing trauma. Hypothermia produces a number of physiologic derangements which worsen the effects of major injury. Several relevant enzyme systems begin to lose efficiency as their ambient temperature falls. For example, the myocardium, which is dependent on the function of membrane-channel type enzymes for normal electrical function, shows a predictable series of atrial followed by ventricular arrhythmias as core temperature falls below 34° C. Cardiac output is further compromised by poor function of intrinsic myocardial components, with bovine myocardium showing a linear decrease in developed tension with decreasing temperature.

Hypothermia also exacerbates hemorrhagic shock in multiple ways. The onset of coagulopathy which accompanies hypothermia, has been shown to result from malfunction of both clotting factors and platelets.

While profound hypothermia may be tolerated by immersion or cardiac surgery patients, the presence of hypothermia in trauma patients predicts significantly higher mortality. Mortality doubles for heterogeneous groups of trauma patients at 34° C., and survival after trauma is very rare when the core temperature falls below 32° C. This effect is greater for more severely injured patients.

The development of hypothermia comes from several factors. Body heat is convectively lost to the environment, and this effect is enhanced by bleeding or the presence of large surface area burns. The body loses both central thermoregulation and peripheral shivering after traumatic injury. Less heat is produced peripherally as perfusion decreases in shock.

The administration of intravenous fluids is used in trauma resuscitation. The administration of fluid at ambient temperature, however, induces hypothermia. This condition is worse in more severely injured patients, who require the most fluid and have the least ability to tolerate the additional insult of decreased core temperature. Hypothermia and mortality clearly increase after the administration of five liters of crystalloid or five units of packed red blood cells, and the onset of hypothermia increases the incidence of coagulopathy in injured patients, particularly in the presence of acidosis.

As used herein, the term "biocompatible fluid" refers to any fluid that is appropriate for infusion into the human body, including normal saline and its less concentrated derivatives, Ringer's lactate, and hypertonic crystalloid solutions; blood and fractions of blood including plasma, platelets, albumin and cryoprecipitate; intravascular volume expanding blood substitutes including hetastarch, polymerized hemoglobin, perfluorocarbons; medications reconstituted with saline or sterile water; and medical gasses including air, oxygen, helium, nitric oxide, and combinations thereof.

Prior art methods of treating hypothermia include direct intravenous fluid warming. The fluid that is warmed may be the blood other biocompatible liquid.

Prior art devices used to warm one or more biocompatible fluids for use in the treatment of trauma have used electricity as their heating source. These systems are referred to herein as "biocompatible liquid infusion systems." Electrically heated biocompatible fluid infusion systems have several drawbacks. If the source of electrical energy is alternating current from a central generating station, the unit can then only be used in locations where such alternating current is available. This significantly limits the locations where the units may be used. Locations such as non-industrialized nations or battlefield locations are likely not have readily available sources of alternating current to power such systems.

Batteries may also be used to generate electrical energy. It is believed that sufficient power to heat a single liter of fluid to 20° C. within a ten minute time period would require a rechargeable battery the size and weight of a large laptop computer. In such a case, the weight of the battery would exceed the weight of a liter of saline fluid. The size and weight of such a unit would limit its portability. Additionally, the battery would require recharging after each liter of biocompatible fluid is delivered.

The present invention overcomes the limitations of prior art biocompatible fluid infusion systems by providing a biocompatible liquid infusion system that is not dependent upon electrical energy as a heat source. The present invention is light enough and compact enough to be used in field hospital environments which are remotely located from large central hospitals and from sources of alternating current. The present invention may also be used to warm air delivered to a patent via a ventilation circuit.

SUMMARY OF THE INVENTION

The present invention is directed toward a portable biocompatible fluid warming system that may be used for infusing biocompatible liquids into a patient for the treatment of trauma. The present invention uses heat from hydrocarbon combustion. Hydrocarbon combustion can take place in the absence of an open flame. As an example, in one embodiment, the present invention may be used with a gaseous hydrocarbon such as butane which is allowed to flow onto a platinum mesh and then ignited. The butane combines with oxygen and liberates heat which then heats the platinum mesh. In this embodiment, the temperature of the mesh stabilizes at the ignition temperature of the butane, thereby allowing combustion to occur on the surface of the platinum mesh.

The present invention functions as a heat exchanger which takes the heat resulting from the hydrocarbon combustion process described above and transfers this heat to a biocompatible liquid.

DESCRIPTION OF THE PREFERRED EMBODIMENTS

Figure 2:
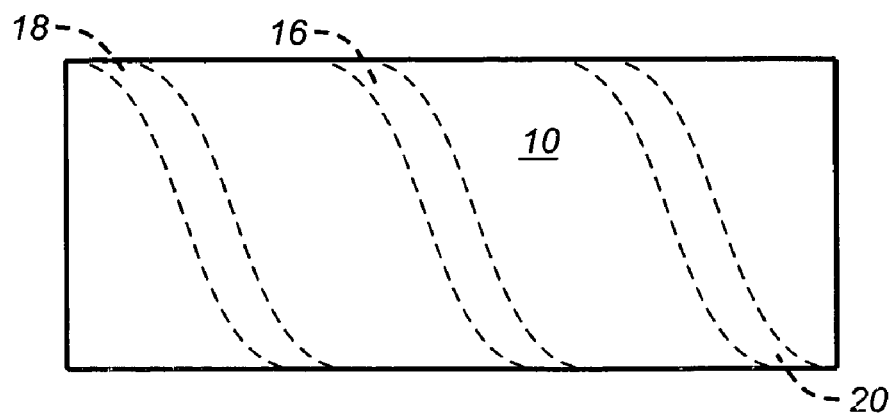
FIG. 2 is an isometric view of one embodiment of the present invention.
Figure 3:
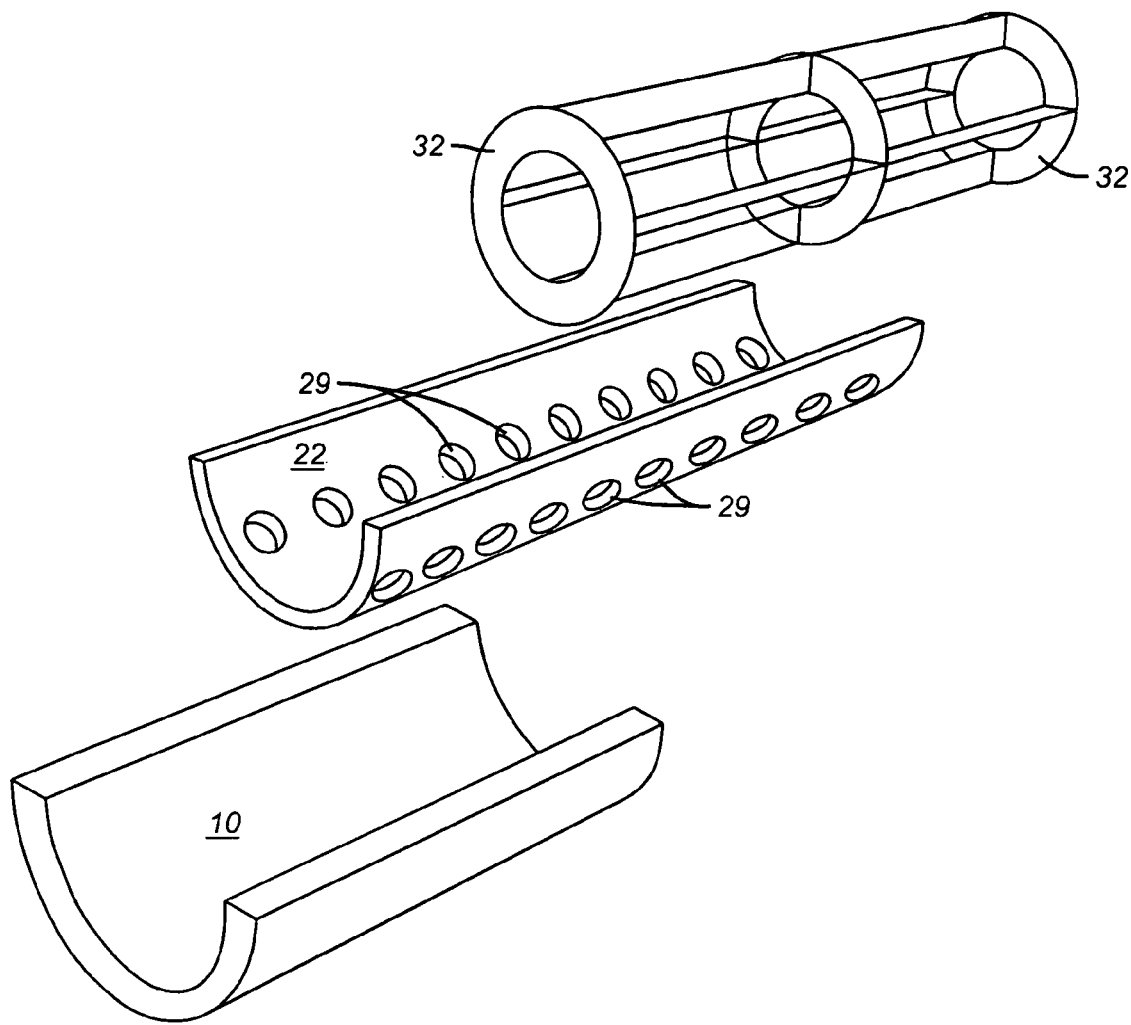
FIG. 3 is an exploded isometric view of one embodiment of the present invention.

In a preferred embodiment, the present invention is directed toward a portable warmer of a biocompatible fluid comprising an outer steel housing 10 comprising a first outer diameter 12, a first inner diameter 14, and at least one flow channel 16 located between the first inner diameter and the first outer diameter as shown in FIGS. 2 and 3.

The term "diameter" as used herein refers to the length of an axis which bisects a cross sectional area of the housing. For cylindrical geometries the diameter is constant at a given point along the longitudinal axis of the cylindrical housing at various azimuths. For noncylindrical geometries the diameter at a given point along the longitudinal axis of the housing may vary as a function of the azimuth.

In a preferred embodiment, the outer diameter of the steel housing is no more than 20 centimeters. In another preferred embodiment, the outer housing is cylindrical. In another preferred embodiment, the outer housing is made of stainless steel.

Figure 1:
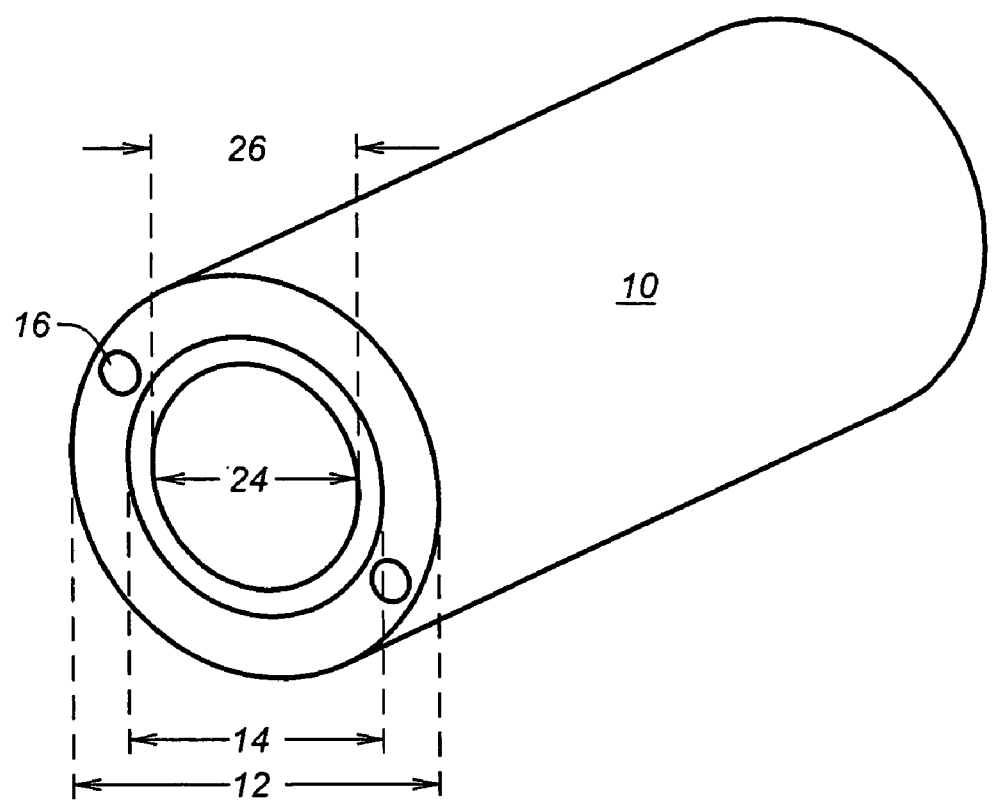
FIG. 1 is a side cutaway view of one embodiment of the outer housing of the present invention.

The flow channel comprises an inlet section 18 and an outlet section 20, as shown in FIG. 1. In a preferred embodiment, the flow channel is helical, as shown in FIG. 1. In another preferred embodiment, the mass of the portable warmer described herein is less than or equal to two kilograms.

This embodiment of the invention further comprises an inner aluminum housing 22 having a second outer diameter 24 sized to fit snugly within said outer housing and an inner wall defining a second inner diameter 26 and an internal volume as shown in FIGS. 2 and 3. In the preferred embodiment depicted in FIG. 2, the internal volume defined by inner diameter 26 extends longitudinally the length of outer housing 10. In a preferred embodiment both the outer and inner housings are cylindrical. In a preferred embodiment, the inner housing comprises at least two ports 29 to permit fluid flow between regions on opposite sides of the inner housing as shown in FIG. 3. In another preferred embodiment, the inner housing comprises at least two grooves in which fluid can flow.

Figure 5:
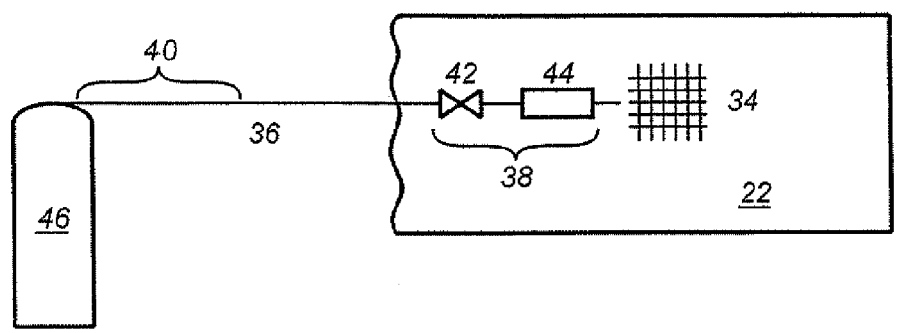
FIG. 5 is a side view of the gas delivery and ignition components of the present invention.

This preferred embodiment further comprises a multiplicity of heat transfer protrusions 32 affixed to the inner wall as shown in FIG. 3. In one preferred embodiment, the heat transfer protrusions are fins. In another preferred embodiment, the heat transfer protrusions are ring like disks as shown in FIG. 3. In a preferred embodiment, the invention further comprises a metallic mesh 34 located within the internal cylindrical volume as shown in FIG. 5. In a preferred embodiment, the metallic mesh is made from a metal selected from the group consisting of palladium and platinum.

This invention further comprises a gas delivery line 36 comprising a distal end region 38 located within the internal volume and a proximal end region 40 located outside the internal volume as shown in FIG. 5. A valve 42 is located in the gas delivery line. In a preferred embodiment, the valve is a needle valve.

The invention further comprises a spark igniter 44 located in the internal volume and situated close enough to the valve such that when the valve is open and gas flows through the gas delivery line and the valve into the internal volume, the igniter can ignite the gas and cause the wire mesh to be heated to a temperature in excess of 420° C., as shown in FIG. 5. In a preferred embodiment, the invention further comprises a source of combustible gaseous hydrocarbon 46 in fluid communication with the proximal end of the gas delivery line as shown in FIG. 5. In a preferred embodiment, the gaseous hydrocarbon is selected from the group consisting of methane, ethane, propane, and butane.

Figure 4:
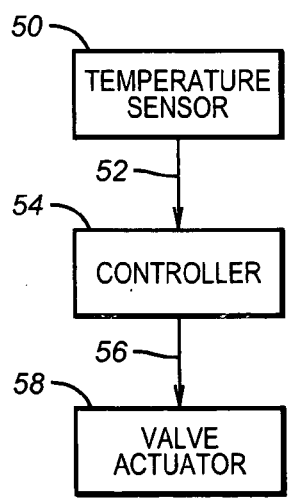
FIG. 4 is a block diagram of the process control instrumentation of a preferred embodiment of the present invention.

Another embodiment of the present invention comprises process controls for controlling the temperature of the fluid output from the portable fluid warmer. In this embodiment, the invention further comprises a temperature sensor 50 positioned to sense the temperature of a fluid flowing through the outlet section of the flow channel and to transmit a temperature signal 52 indicative of the temperature of a fluid flowing through the outlet section of the flow channel as shown in FIG. 4. In a preferred embodiment, the temperature sensor is selected from the group consisting of a thermistor, a thermocouple, and a solid state thermal sensor.

Figure 6:
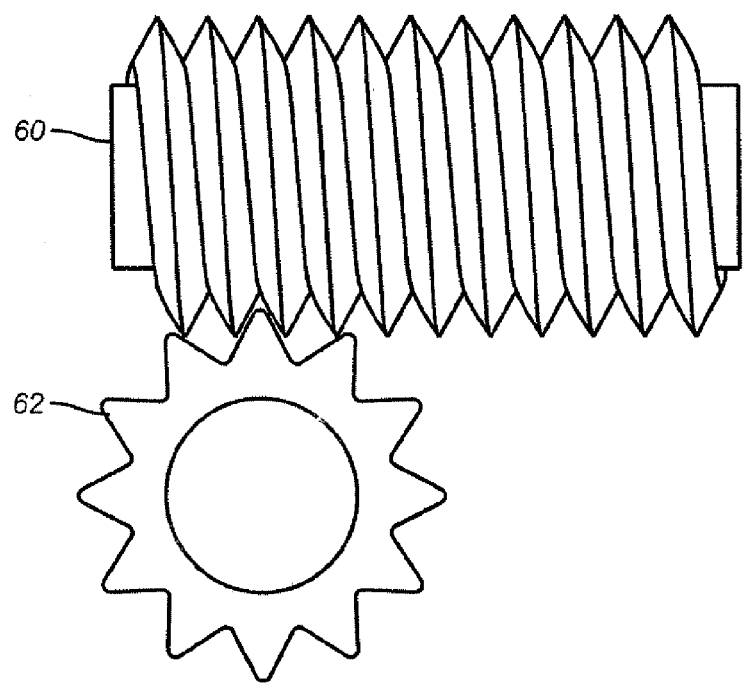
FIG. 6 is a side view of one embodiment of the actuator of the present invention.

In another preferred embodiment, the invention further comprises a controller 54 operatively connected to receive the temperature signal from the sensor and transmit a control signal 56 responsive to the temperature signal as shown in FIG. 4. In one preferred embodiment, the controller is a microcontroller. In another preferred embodiment, the controller is an analog controller. In a preferred embodiment, when the temperature signal indicates that the temperature of the fluid flowing through the outlet section of flow channel exceeds a preselected temperature threshold, a control signal to increase the degree of closure of the valve is generated. In another preferred embodiment, the actuator comprises worm gear 60 mechanically coupled to a spur gear 62 as shown in FIG. 6. In this embodiment, the spur gear is mechanically coupled to the valve.

In this embodiment, the invention further comprises a valve actuator 58 operatively connected to the valve and to the controller to control the degree of closure of the valve in response to the control signal as shown in FIG. 4. In a preferred embodiment, the valve actuator is coupled to receive the control signal from the controller. In a preferred embodiment, the valve actuator is a servo-controller.

In other embodiments, temperature may be regulated by controlling fuel flow into the inner cylinder. Additionally, temperature may be controlled by mixing small amounts of unheated fluid with the heated fluid exiting the portable warming device. In another embodiment, fluid temperature may be controlled by changing the thermal conductance of the layer between the inner cylinder and the flow channels.

The foregoing disclosure and description of the invention are illustrative and explanatory. Various changes in the size, shape, and materials, as well as in the details of the illustrative construction may be made without departing from the spirit of the invention.

What is claimed is:

1. A portable warmer of a biocompatible fluid comprising:
   (a) an outer stainless steel housing comprising a first outer diameter, a first inner diameter, and at least one flow channel located between said first inner diameter and said first outer diameter, said flow channel comprising an inlet section and an outlet section;
   (b) an inner aluminum housing having a second outer diameter sized to fit snugly within said outer housing and an inner wall defining a second inner diameter and an internal volume;
   (c) a multiplicity of heat transfer protrusions affixed to said inner wall;

(d) a metallic mesh located within said internal cylindrical volume;
(e) a gas delivery line comprising a distal end region located within said internal volume and a proximal end region located outside said internal volume;
(f) a valve located in the distal end region of said gas delivery line; and
(g) a spark igniter located in said internal volume and situated close enough to said valve such that when said valve is open and gas flows through said gas delivery line and said valve into said internal volume, the igniter can ignite the gas and cause the wire mesh to be heated to a temperature in excess of 420 degrees Centigrade.

2. The device of claim 1, wherein the metallic mesh is made from a metal selected from the group consisting of palladium and platinum.

3. The device of claim 1, wherein said flow channel is helical.

4. The device of claim 1, wherein the mass of the portable warmer is less than or equal to 2 kilograms.

5. The device of claim 1, wherein the outer diameter of the steel housing is no more than 20 centimeters.

6. The device of claim 1, wherein said heat transfer protrusions are disc like rings.

7. The device of claim 1, further comprising a source of combustible gaseous hydrocarbon in fluid communication with said proximal end.

8. The device of claim 7, wherein said gaseous hydrocarbon is selected from the group consisting of methane, ethane, propane, and butane.

9. The device of claim 1, further comprising:
(a) a temperature sensor positioned to sense the temperature of a fluid flowing through the outlet section of said flow channel and to transmit a temperature signal indicative of the temperature of a fluid flowing through the outlet section of said flow channel;
(b) a controller operatively connected to receive said temperature signal from said sensor and to transmit a control signal responsive to said temperature signal; and
(c) a valve actuator operatively connected to said valve and to said controller to control the degree of closure of said valve in response to said control signal.

10. The device of claim 9, wherein said temperature sensor is selected from the group consisting of a thermistor, a thermocouple and a solid state thermal sensor.

11. The device of claim 9, wherein a control signal to increase the degree of closure of said valve is generated when the temperature signal indicates that the temperature of said fluid flowing through the outlet section of said flow channel exceeds a preselected temperature threshold.

12. The device of claim 11, wherein the controller is a microcontroller and the valve actuator is a servo-controller.

13. The device of claim 9, wherein the controller is an analog controller.

14. The device of claim 9, wherein said actuator comprises a worm gear mechanically coupled to a spur gear.

15. The device of claim 1, wherein said inner housing comprises at least two ports to permit fluid flow between regions on opposite sides of said inner cylinder.

16. The device of claim 1, wherein said inner housing comprises at least two grooves in which fluid can flow.

17. The device of claim 1, wherein said outer housing is cylindrical.

18. The device of claim 17, wherein said inner housing is cylindrical.

19. A portable warmer of a biocompatible fluid comprising:
(a) an outer stainless steel cylinder comprising a first outer diameter, a first inner diameter, and at least one flow channel located between said first inner diameter and said first outer diameter, said flow channel comprising an inlet section and an outlet section;
(b) an inner aluminum cylinder having a second outer diameter sized to fit snugly within said outer cylinder and an inner wall defining a second inner diameter and an internal cylindrical volume;
(c) a multiplicity of heat transfer protrusions affixed to said inner wall;
(d) a metallic mesh located within said internal cylindrical volume;
(e) a gas delivery line comprising a distal end region located within said internal volume and a proximal end region located outside said internal volume;
(f) a valve located in the distal end region of said gas delivery line; and
(g) a spark igniter located in said internal volume and situated close enough to said valve such that when said valve is open and gas flows through said gas delivery line and said valve into said internal volume, the igniter can ignite the gas and cause the wire mesh to be heated to a temperature in excess of 420 degrees Centigrade.

20. The device of claim 19, further comprising:
(a) a temperature sensor positioned to sense the temperature of a fluid flowing through the outlet section of said flow channel and to transmit a temperature signal indicative of the temperature of a fluid flowing through the outlet section of said flow channel;
(b) a controller operatively connected to receive said temperature signal from said sensor and to transmit a control signal responsive to said temperature signal; and
(c) a valve actuator operatively connected to said valve and to said controller to control the degree of closure of said valve in response to said control signal.

* * * * *